(12) United States Patent
Dombeck

(10) Patent No.: US 8,741,271 B2
(45) Date of Patent: Jun. 3, 2014

(54) ANTIMICROBIAL COMPOSITIONS CONTAINING ESSENTIAL OILS

(76) Inventor: Danice Dombeck, Prairie du Sac, WI (US)

(*) Notice: Subject to any disclaimer, the term of this patent is extended or adjusted under 35 U.S.C. 154(b) by 5 days.

(21) Appl. No.: 13/095,223

(22) Filed: Apr. 27, 2011

(65) Prior Publication Data

US 2012/0014896 A1 Jan. 19, 2012

Related U.S. Application Data

(60) Provisional application No. 61/365,590, filed on Jul. 19, 2010.

(51) Int. Cl.
| | | |
|---|---|---|
| *A61K 8/00* | (2006.01) | |
| *A61K 8/18* | (2006.01) | |
| *A61Q 15/00* | (2006.01) | |
| *A01N 65/00* | (2009.01) | |
| *A61K 36/889* | (2006.01) | |
| *A61K 36/54* | (2006.01) | |
| *A61K 8/97* | (2006.01) | |
| *A61Q 5/00* | (2006.01) | |
| *A61Q 9/00* | (2006.01) | |
| *A61K 36/537* | (2006.01) | |
| *A61K 36/534* | (2006.01) | |
| *A61K 36/899* | (2006.01) | |

(52) U.S. Cl.
USPC .............. 424/65; 424/727; 424/739; 424/74; 424/746; 424/747; 424/750

(58) Field of Classification Search
CPC ....... A01N 65/00; A01N 65/22; A01N 65/24; A01N 65/28; A01N 65/36; A01N 65/44; A01N 37/36; A01N 2300/00; A61K 8/922; A61K 2800/30; A61Q 15/00; A61Q 17/005
USPC ............. 424/65, 727, 739, 74, 746, 747, 750
See application file for complete search history.

(56) References Cited

U.S. PATENT DOCUMENTS

| | | | |
|---|---|---|---|
| 4,966,754 A * | 10/1990 | Purohit et al. ................. | 424/401 |
| 6,846,498 B2 | 1/2005 | Death et al. | |
| 7,148,187 B1 * | 12/2006 | Simon et al. ................... | 510/235 |
| 7,439,218 B2 | 10/2008 | Bowker | |
| 7,465,697 B1 | 12/2008 | Death | |
| 7,578,970 B2 | 8/2009 | Bowker | |
| 2003/0083212 A1 | 5/2003 | Willard et al. | |
| 2006/0165739 A1 * | 7/2006 | Komesvarakul et al. ..... | 424/401 |
| 2008/0045491 A1 | 2/2008 | Fitchmun | |
| 2008/0253976 A1 | 10/2008 | Scott et al. | |
| 2009/0004122 A1 | 1/2009 | Modak et al. | |
| 2009/0035228 A1 | 2/2009 | Modak et al. | |
| 2009/0175806 A1 | 7/2009 | Modak et al. | |
| 2009/0232905 A1 | 9/2009 | Weiss et al. | |
| 2009/0285886 A1 * | 11/2009 | Van Beek ...................... | 424/451 |

OTHER PUBLICATIONS

"Excellent Aromatherapy Guide" http://excellentaromatherapyguide.com/blog/aromatherapy-essential-oil-palmarosa.html/ web pages printed on Jun. 17, 2010 (5 pages).
Esoteric Oils "Palmarosa essential oil information", http://essentialoils.co.za/essential-oils/palmarosa.htm, web pages printed on Jun. 17, 2010 (6 pages).
CleanWell "All-Natural Hand Sanitizer" http://cleanwelltoday.com/, web pages printed on Jun. 4, 2010 (4 pages).
Ruhme, Jill "Time Kill Assay for Antimicrobial Agents", ATS Labs, project No. A08736, study completed Jan. 12, 2010, (6 pages).
Arcade BeautiSeal Sampling System® "Gold Bond Ultimate® Hand Sanitizer Moisturizer" sample and coupon, 2010 (1 page).
Nichol, Katie "Chattem skin care brand launches alcohol-free Hand Sanitizer Moisturizer", Jan. 28, 2010, http://www.cosmeticdesign.com/Products-Markets/Chattem-skin-care..., web page printed Jun. 4, 2010 (1 page).

* cited by examiner

*Primary Examiner* — Robert T Crow
*Assistant Examiner* — Doan Phan
(74) *Attorney, Agent, or Firm* — Foley & Lardner LLP

(57) ABSTRACT

Compositions for cleaning, disinfecting and sanitizing are described. The compositions comprise essential oils and are stable, non-toxic and environmentally sustainable. Also disclosed are deodorants and scalp refreshers having these properties.

22 Claims, No Drawings

ANTIMICROBIAL COMPOSITIONS CONTAINING ESSENTIAL OILS

CROSS-REFERENCE TO RELATED APPLICATIONS

This application claims priority to U.S. Provisional Application No. 61/365,590, filed Jul. 19, 2010, the entire contents of which are hereby incorporated by reference in their entirety.

TECHNICAL FIELD

The present technology relates generally to sanitizing and deodorant products. In particular, the present technology relates to hand sanitizing and deodorant products containing essential oils.

BACKGROUND

The following description is provided to assist the understanding of the reader. None of the information provided or references cited is admitted to be prior art.

Microbial entities such as bacteria, viruses, spores, algae, and fungi are the common agents of disease, and a large amount of pharmaceutical research and a wide variety of products have been developed to counteract the conditions they cause. There exist several contemporary compositions and methods for reducing and/or eliminating the formation of harmful microbial entities. Natural health care and skin care products having antimicrobial properties have gained popularity for their effectiveness, safety, and value for money. These antimicrobial products find application in sanitizing compositions, deodorants, cleaning compositions, disinfectants, personal care products, home care products, cosmetics and the like. However, many of the known natural antimicrobial products are associated with disadvantages, such as, for example, having selective activity, i.e., some of these products work well against bacteria, but not against viruses or fungi, while some will work only against certain strains of bacteria. Moreover, many products lose their activity over a period of time as the pathogens become resistant to the product. There is, therefore, a need for a safe, natural antimicrobial product which provides protection against a broad spectrum of pathogens including viruses, bacteria and fungi without losing their effectiveness over a period of time.

There has been a dramatic increase in the concern for sanitizing, both of person and property, since the emergence of Swine flu. Hand sanitizing equipment is now routinely found in many public locations and private offices as well as in homes. A majority of the hand sanitizing products available in the market are alcohol based products which contain more than 60 percent alcohol concentration that is deemed necessary to kill most harmful bacteria and viruses. The alcohol present in hand sanitizers can also cause skin dryness, leading to broken skin, which exposes the body to the same contagions users are trying to prevent. There is also a concern that hand sanitizers could be a health hazard to the young if ingested in large amounts due to the alcohol content. The high alcohol content also makes this type of sanitizer very flammable and, therefore, must be kept away from open flames and other fire hazard environments.

Alternatives to alcohol based hand sanitizers are also available in the market. Some of these include chemicals such as benzalkonium chloride or triclosan, which are known to have serious side effects such as asthma, dermatitis, skin irritations, hypersensitivity and other immune dysfunctions. Severe health hazards of these chemicals including circulatory collapse, convulsions, coma, damage to liver, kidneys, heart, and lungs, paralysis, sterility, brain hemorrhages, hormonal disruption and death are also known. These products can also be a biohazard as these chemical compounds are not biodegradable. New sanitizing products must, therefore, find a compromise between greater antimicrobial efficacy and lower heath hazards and biohazards. Most of the presently available commercial products fail to optimize either attribute.

There is an increasing need for antimicrobial products effective against a broad range of pathogens which significantly reduce the harmful health and environmental hazards associated with other products without compromising their quality, stability and performance.

SUMMARY

In accordance with one aspect, the present technology relates to antimicrobial compositions which include essential oils. In one embodiment, at least one essential oil in the composition is palmarosa oil. In some embodiments, the essential oils comprise palmarosa oil and tea tree oil. In one aspect, the present technology provides an antimicrobial composition comprising one or more essential oils and one or more fruit acids, wherein (a) at least one essential oil is palmarosa oil, (b) the composition possesses antimicrobial activity, and (c) the composition is alcohol-free. In some embodiments, the antimicrobial composition further comprises tea tree oil.

In some embodiments, the one or more essential oils are selected from the group consisting of palmarosa oil, tea tree oil, jojoba oil, coconut oil, lavender oil, clary sage oil, peppermint oil, spearmint oil and cinnamon oil.

In some embodiments, the fruit acid is selected from the group consisting of citric acid, glycolic acid, lactic acid, malic acid, tartaric acid and acetic acid. In some embodiments, the fruit acid is citric acid.

In some embodiments, the composition further includes one or more components selected from a group consisting of emollients, moisturizers, preservatives, thickeners, fragrance agents and homogenizers. In some embodiments, the emollient is lanolin. In some embodiments, the moisturizer is coconut oil. In some embodiments, the moisturizer/emollient is jojoba oil. In some embodiments, the thickener is xanthan gum.

In some embodiments, the composition is a hand-sanitizer. In other embodiments, the composition is a deodorant. In some embodiments, the composition is a dry-shampoo or a scalp refresher.

In some embodiments, the antimicrobial composition includes the following components: palmarosa oil, tea tree oil, jojoba oil, coconut oil, cinnamon oil, citric acid, lanolin, xanthan gum, and water. In some embodiments, the antimicrobial composition includes peppermint oil and/or spearmint oil.

In one aspect the present technology provides an antimicrobial composition which includes (a) about 0.5% to about 2% by volume of palmarosa oil, (b) about 0.3% to about 2% by volume of tea tree oil, (c) about 0.5% to about 2% by volume of jojoba oil, (d) about 1% to about 5% by volume of coconut oil, (e) about 0.1% to about 1% by volume of cinnamon oil, (f) about 0.1% to about 1% by volume of peppermint oil, (g) about 0.5% to about 2% by volume of citric acid, and (h) about 0.5% to about 2% by volume of lanolin (i) about 0.3% to about 2% xanthan gum. In some embodiments, the composition comprises a hand sanitizer.

In some embodiments, the ratio of the components of the antimicrobial hand-sanitizer composition is substantially: Palmarosa oil (4): Tea tree oil (2): Jojoba oil (4): Coconut oil (10): Cinnamon oil (1): Citric acid (4): Lanolin (4): Xanthan gum (2): and Peppermint oil (1). In some embodiments, the composition comprises a hand sanitizer.

In another aspect, the present technology provides a deodorant composition. In some embodiment, the deodorant composition is antibacterial. In some embodiments, the deodorant composition includes one or more of palmarosa oil and tea tree oil. In some embodiments, the deodorant composition further includes jojoba oil, citric acid and sodium bicarbonate. In some embodiments, the deodorant composition includes a fragrance agent. In some embodiments, the fragrance agent is selected from lavender oil, spearmint oil, peppermint oil or a combination thereof. In some embodiments, the fragrance agent is lavender oil and spearmint oil. In some embodiments, the fragrance agent is lavender oil and peppermint oil. In some embodiments, the fragrance agent is peppermint oil and spearmint oil.

In some embodiments, the deodorant composition includes (a) about 0.5% to about 2% by volume of palmarosa oil, (b) about 1% to about 4% by volume of jojoba oil, (c) about 0.5% to about 2% by volume of lavender oil, (d) about 0.3% to about 2% by volume of citric acid. In some embodiments, clary sage oil is added.

In some embodiments, the deodorant composition includes (a) about 0.5% to about 2% by volume of tea tree oil, (b) about 0.5% to about 2% by volume of palmarosa oil, (c) about 0.5% to about 2% by volume of jojoba oil, (d) about 0.5% to about 2% by volume of coconut oil, (e) about 0.3% to about 2% by volume of peppermint oil or spearmint oil, (e) about 0.8% to about 3% by volume of lavender oil, and (f) about 0.5% to about 2.5% by volume of citric acid.

In some embodiments, the deodorant composition includes (a) about 0.5% to about 2% by volume of tea tree oil, (b) about 0.5% to about 2% by volume of palmarosa oil, (c) about 0.5% to about 2% by volume of jojoba oil, (d) about 0.5% to about 2% by volume of coconut oil, (e) about 0.3% to about 2% by volume of peppermint oil, (e) about 0.1% to about 2% by volume of spearmint oil, and (f) about 0.5% to about 2.5% by volume of citric acid.

In some embodiments, the deodorant composition further includes a thickener. In some embodiments, the thickener is xanthan gum. In some embodiments, the deodorant composition further includes an odor-neutralizer. In some embodiments, the odor-neutralizer is sodium bicarbonate.

In another aspect, the present technology provides a scalp refresher composition which includes: sweet orange oil, grapefruit oil, lavender oil, rosemary oil, sandalwood oil, peppermint oil, and citric acid.

In some embodiments, the scalp refresher composition includes: (a) about 0.8% to about 3% by volume of sweet orange oil, (b) about 0.5% to about 2% by volume of grapefruit oil, (c) about 0.1% to about 2% by volume of lavender oil, (d) about 0.05% to about 1% by volume of rosemary oil, (e) about 0.05% to about 1% by volume of sandalwood oil, (f) about 0.05% to about 1% by volume of peppermint oil, and (g) about 0.5% to about 2.5% by volume of citric acid.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

In the following detailed description, the illustrative embodiments described in the detailed description, figures, and claims are not meant to be limiting. Other embodiments may be utilized, and other changes may be made, without departing from the spirit or scope of the subject matter presented here. In the description that follows, a number of terms are used extensively. The terms described below are more fully understood by reference to the specification as a whole. Units, prefixes, and symbols may be denoted in their accepted SI form.

The terms "a" and "an" as used herein mean "one or more" unless the singular is expressly specified. Thus, for example, reference to "an oil" includes a mixture of two or more oils, as well as a single oil.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to, plus or minus 10% of the particular term.

As used herein, the term "contacting" encompasses the placement of the antimicrobial product on to the skin surface.

As used herein, the term "combining" refers to the mixing or admixing of ingredients in a composition or formulation.

As used herein, the term "ingredient" refers to any essential oil, fruit acid or additive, whether of chemical or plant origin, that can be used in the compositions. Other ingredients that promote the antimicrobial properties of the compositions can be selected by those of skill in the art.

The term "synergistic" implies that the antimicrobial effect of the combination is greater than the sum of the antimicrobial effects of the individual components.

The present technology provides compositions and products which include essential oils and possesses antimicrobial activity and methods of using these compositions to disinfect a surface. In one aspect, an aqueous composition which includes one or more essential oils and one or more fruit acids, where at least one oil is palmarosa oil and wherein the composition possesses antimicrobial activity, is provided.

As used herein, "essential oils" or "EOs" will be understood by persons of ordinary skill in the art to be volatile oils obtained from plant or animal sources, or their synthetic equivalents, and are composed of complex mixtures of several constituents as monoterpenes and sesquiterpene hydrocarbons, monoterpene and sesquiterpene alcohols, esters, ethers, aldehydes, ketones, oxides and the like. Examples of EOs include, but are not limited to, palmarosa oil, jojoba oil, tea tree oil, clary sage oil, coconut oil, lavender oil, cinnamon oil, geranium oil, lemon oil, lime oil, orange oil, sweet orange oil, grapefruit oil, rosemary oil, aniseed oil, eucalyptus oil, camphor oil, calamus oil, cedarwood oil, citronella oil, mint oil, nutmeg oil, vetiver oil, wintergreen oil, ylang-ylang oil, neroli oil, sage oil, sandalwood oil, frankincense oil, ginger oil, peppermint oil, wintergreen oil, jasmine absolute, spearmint oil, patchouli oil, rosewood oil, vanilla oil, lemongrass oil, basil oil, bergamot oil, balsam oils, tangerine oil, Hinoki oil, Hiba oil, ginko oil, eucalyptus oil, pomegranate oil, manuka oil, and *calendula* oil. The above list is not exclusive and one skilled in the art will readily recognize other essential oils from the several hundred EOs known in the art which can find use in the present compositions and methods.

Essential oils are derived from a wide variety of plant materials such as flowers, fruits, seeds, leaves, stalks, barks, roots and rhizomes. One of the most satisfactory aspects of using essential oils medicinally and cosmetically is that they enter and leave the body with great efficiency, leaving no toxins behind. However, formulation of essential oils into ready-to-use products is difficult because these oils are immiscible with water due to their hydrophobic nature.

Manufacturers have often resorted to using harsh solvents and synthetic surfactants to facilitate formation of homogeneous aqueous mixtures of essential oils, thereby eroding the benefits of using natural essential oils. Further, not all essential oils are without demerits. For example, the so called "hot oils" such as thyme, oregano, cinnamon, clove and mountain savory are high in phenols that may irritate the skin. Long-term stability of products containing essential oils is also an issue. This calls for discovery of effective combination of safe and gentle essential oils and non-toxic, biodegradable surfactants which will result in natural products having high efficacy, improved stability and ease of formulation.

Palmarosa oil is an essential oil which is known to moisturize the skin while balancing the hydration levels and stimulating cell regeneration. More importantly, it helps to balance the production of sebum and keep the skin supple and elastic and is valuable for use with acne, dermatitis, preventing scarring, rejuvenating and regenerating the skin. Palmarosa oil is also known to help clear up minor infections and prevent ugly scarring in healing wounds. On cellular level, it helps with the formation of new tissue and, for that reason, is great for rejuvenating and regenerating the skin.

In some embodiments of the present technology, the EO is selected from one or more EOs from the group consisting of palmarosa oil, tea tree oil, jojoba oil, coconut oil, lavender oil, clary sage oil and cinnamon oil. It was found by the inventor that all of these oils, particularly palmarosa oil, have antiseptic, antimicrobial, antiviral, bactericide, cytophylactic and hydrating properties and are, therefore, effectively used in the present antimicrobial compositions. In some embodiments, palmarosa oil is also used in deodorant and scalp refresher compositions.

Mixtures of one or more EOs are encompassed by the present invention. An EO for use in the present compositions may be obtained from its natural source or may be chemically synthesized. For example, palmarosa oil can be extracted from the dried grass of *Cymbopogon martinii* harvested before it flowers by steam distillation. Tea tree oil is obtained by steam distillation of the leaves of *Melaleuca alternifolia*, a plant native to Australia. Jojoba oil can be obtained by extraction of jojoba (*Simmondsia chinensis*) seeds with an organic solvent. Clary sage oil can be obtained from the leaves and buds of the clary sage plant (*Salvia Sclarea*) by steam distillation. Coconut oil can be extracted from the kernel or meat of matured coconut harvested from the coconut palm (*Cocos nucifera*). Lavender oil can be obtained by distillation from the flower spikes of certain species of lavender. Cinnamon oil can be extracted by steam distillation from the bark or the leaves and twigs of the Lauraceae botanical plant family. These essential oils are also commercially available.

Fruit acids which may be used in the present compositions and methods include, but are not limited to, citric acid, oxalic acid, acetic acid, glycolic acid, lactic acid, malic acid, tartaric acid, salicylic acid, and boric acid or mixtures thereof. These fruit acids may be obtained from various natural sources, i.e., fruits, or chemically synthesized using methods known in the art. For example, some fruits in which citric acids and citrates naturally occur include lemons, oranges, grapefruits, limes, quinces, gooseberries, strawberries, raspberries, currants and cranberries. In some embodiments, the fruit acid is selected from the group consisting of citric acid, glycolic acid, lactic acid, malic acid, tartaric acid and acetic acid. In some embodiments, the fruit acid is citric acid.

In various non-limiting embodiments, different concentrations of essential oils may be used. In some embodiments, the concentration of each essential oil in the final products may range from about 0.01% to about 25% (w/w). In some embodiments, the concentration of each essential oil may range from about 0.1% to about 20% (w/w). In some embodiments, the concentration of each essential oil ranges from about 0.5% to about 15% (w/w). These concentrations may be increased in stock solutions intended for dilution where the above ranges provide for the concentration after dilution.

In some non-limiting embodiments, different concentrations of essential oils may be used. In some embodiments, the concentration of each essential oil in the final products may range from about 0.01% to about 25% (v/v). In some embodiments, the concentration of each essential oil may range from about 0.1% to about 20% (v/v). In some embodiments, the concentration of each essential oil ranges from about 0.5% to about 15% (v/v). In some embodiments, the concentration of each essential oil ranges from about 0.5% to about 2% (v/v), from about 1% to about 5% (v/v), from about 1% to about 4% (v/v) from about 0.1% to about 1% (v/v), from about 0.1% to about 2%, from about 0.3% to about 2% (v/v), from about 0.8% to about 3% (v/v), from about 0.05% to about 1% (v/v). These concentrations may be increased in stock solutions intended for dilution where the above ranges provide for the concentration after dilution.

In some embodiments, specific concentrations of individual essential oils, as well as fruit acids, are important for providing compositions having improved antimicrobial activity, stability and malleability to be formulated as solid or liquid formulations. Thus, in some embodiments, the amount of palmarosa oil in the composition is in the range of about 0.01% to about 15% by weight. In some embodiments, the amount of palmarosa oil in the composition is in the range of about 0.1% to about 10% by weight. In some embodiments, the amount of palmarosa oil in the composition is in the range of about 1% to about 5% by weight. In some embodiments, the amount of palmarosa oil in the composition is in the range of about 2% to about 4% by weight. In some embodiments, the amount of palmarosa oil in the composition is in the range of about 2.5% to about 3.5% by weight. In some embodiments, the amount of palmarosa oil in the composition is in the range of about 0.01% to about 15% by volume. In some embodiments, the amount of palmarosa oil in the composition is in the range of about 0.1% to about 10% by volume. In some embodiments, the amount of palmarosa oil in the composition is in the range of about 1% to about 5% by volume. In some embodiments, the amount of palmarosa oil in the composition is in the range of about 2% to about 4% by volume. In some embodiments, the amount of palmarosa oil in the composition is in the range of about 2.5% to about 3.5% by volume, or about 0.5% to about 2% by volume.

In some embodiments, the amount of tea tree oil in the composition is in the range of about 0.01% to about 10% by weight. In some embodiments, the amount of tea tree oil in the composition is in the range of about 0.1% to about 5% by weight. In some embodiments, the amount of tea tree oil in the composition is in the range of about 0.5% to about 2.5% by weight. In some embodiments, the amount of tea tree oil in the composition is in the range of about 1% to about 2% by weight. In some embodiments, the amount of tea tree oil in the composition is in the range of about 0.01% to about 10% by volume. In some embodiments, the amount of tea tree oil in the composition is in the range of about 0.1% to about 5% by volume. In some embodiments, the amount of tea tree oil in the composition is in the range of about 0.5% to about 2.5% by volume. In some embodiments, the amount of tea tree oil in the composition is in the range of about 1% to about 2% by volume, or about 0.3% to about 2% by volume, or about 0.5% to about 2% by volume.

In some embodiments, the amount of lavender oil in the composition is in the range of about 0.01% to about 15% by weight. In some embodiments, the amount of lavender oil in the composition is in the range of about 0.1% to about 10% by weight. In some embodiments, the amount of lavender oil in the composition is in the range of about 1% to about 5% by weight. In some embodiments, the amount of lavender oil in the composition is in the range of about 2% to about 4% by weight. In some embodiments, the amount of lavender oil in the composition is in the range of about 2.5% to about 3.5% by weight. In some embodiments, the amount of lavender oil in the composition is in the range of about 0.01% to about 15% by volume. In some embodiments, the amount of lavender oil in the composition is in the range of about 0.1% to about 10% by volume. In some embodiments, the amount of lavender oil in the composition is in the range of about 1% to about 5% by volume. In some embodiments, the amount of lavender oil in the composition is in the range of about 2% to about 4% by volume. In some embodiments, the amount of lavender oil in the composition is in the range of about 2.5% to about 3.5% by volume. In some embodiments, the amount of lavender oil in a composition is in the range of 1% to about 4%, from about 0.8% to about 3%, or from about 0.5% to about 2% by volume.

In some embodiments, the amount of clary sage oil in the composition is in the range of about 0.01% to about 15% by weight. In some embodiments, the amount of clary sage oil in the composition is in the range of about 0.1% to about 10% by weight. In some embodiments, the amount of clary sage oil in the composition is in the range of about 1% to about 5% by weight. In some embodiments, the amount of clary sage oil in the composition is in the range of about 2% to about 4% by weight. In some embodiments, the amount of clary sage oil in the composition is in the range of about 2.5% to about 3.5% by weight. In some embodiments, the amount of clary sage oil in the composition is in the range of about 0.01% to about 15% by volume. In some embodiments, the amount of clary sage oil in the composition is in the range of about 0.1% to about 10% by volume. In some embodiments, the amount of clary sage oil in the composition is in the range of about 1% to about 5% by volume. In some embodiments, the amount of clary sage oil in the composition is in the range of about 2% to about 4% by volume. In some embodiments, the amount of clary sage oil in the composition is in the range of about 2.5% to about 3.5% by volume. In other embodiments, the amount of clary sage oil in the composition is in the range of about 0.1% to about 4%, from about 0.2% to about 3%, or from about 0.3% to about 2% by volume.

Because of its similarity with natural skin and body oils, jojoba oil can be used as a base or carrier oil for certain compositions in the cream, lotion, deodorant or other such forms. Thus, in various embodiments, the amount of jojoba oil in the composition is in the range of about 0.01% to about 15% by weight. In some embodiments, the amount of jojoba oil in the composition is in the range of about 0.1% to about 10% by weight. In some embodiments, the amount of jojoba oil in the composition is in the range of about 2% to about 10% by weight. In some embodiments, the amount of jojoba oil in the composition is in the range of about 1% to about 4% by weight. In some embodiments, the amount of jojoba oil in the composition is in the range of about 2% to about 4% by weight. In some embodiments, the amount of jojoba oil in the composition is in the range of about 2.5% to about 3.5% by weight. In other some embodiments, the amount of jojoba oil in the composition is in the range of about 5% to about 7% by weight. In some embodiments, the amount of jojoba oil in the composition is in the range of about 0.01% to about 15% by volume. In some embodiments, the amount of jojoba oil in the composition is in the range of about 0.1% to about 10% by volume. In some embodiments, the amount of jojoba oil in the composition is in the range of about 2% to about 10% by volume. In some embodiments, the amount of jojoba oil in the composition is in the range of about 1% to about 4% by volume. In some embodiments, the amount of jojoba oil in the composition is in the range of about 2% to about 4% by volume. In some embodiments, the amount of jojoba oil in the composition is in the range of about 2.5% to about 3.5% by volume. In other embodiments, the amount of jojoba oil in the composition is in the range of about 5% to about 7% by volume. In some embodiments, the amount of jojoba oil in the composition is in the range of from about 0.1% to about 5%, from about 1% to about 4%, from about 0.5% to about 2%.

Coconut oil, in addition to its antimicrobial properties, can be used as in the present compositions as an emollient and/or moisturizer. It can also perform as a thickener and an emulsifier depending on its concentration in the composition. Thus, in various embodiments, the amount of coconut oil in the composition is in the range of about 0.01% to about 30% by weight. In some embodiments, the amount of coconut oil in the composition is in the range of about 1% to about 25% by weight. In some embodiments, the amount of coconut oil in the composition is in the range of about 10% to about 20% by weight. In illustrative embodiments, the amount of coconut oil in the composition is in the range of about 14% to about 17% by weight. In various embodiments, the amount of coconut oil in the composition is in the range of about 0.01% to about 30% by volume. In some embodiments, the amount of coconut oil in the composition is in the range of about 1% to about 25% by volume. In some embodiments, the amount of coconut oil in the composition is in the range of about 10% to about 20% by volume. In some embodiments, the amount of coconut oil in the composition is in the range of about 14% to about 17% by volume. In some embodiments, the amount of coconut oil in the composition is in the range of about 0.1 to about 7% from about 1% to about 5%, from about 0.5% to about 3%, or from about 0.5% to about 2% by volume.

Other oils such as lavender oil, peppermint oil and spearmint oil, or a combination thereof can be used as in the present compositions to impart scent or fragrance (e.g., as a fragrance agent). Depending upon the desired level of fragrance, in various embodiments, the amount of a fragrance agent in the composition is in the range of about 0.001% to about 10% by weight. In some embodiments, the amount of peppermint or spearmint oil in the composition is in the range of about 0.01% to about 5% by weight. In some embodiments, the amount of peppermint or spearmint oil in the composition is in the range of about 0.05% to about 3% by weight. In illustrative embodiments, the amount of peppermint or spearmint oil in the composition is in the range of about 0.1% to about 2% by weight. In some embodiments, the amount of a fragrance agent (e.g., lavender oil, peppermint or spearmint oil, etc.) in the composition is in the range of about 0.001% to about 10% by volume. In some embodiments, the amount of fragrance agent e.g., lavender oil, peppermint or spearmint oil in the composition is in the range of about 0.01% to about 5% by volume. In some embodiments, the amount of lavender, peppermint or spearmint oil in the composition is in the range of about 0.05% to about 3% by volume. In illustrative embodiments, the amount of lavender oil, peppermint or spearmint oil in the composition is in the range of about 0.1% to about 2% by volume. In some embodiments, the amount of fragrance agent (e.g., lavender oil, peppermint or spearmint oil) is present in the composition in the range of about 0.1% to about 1%, from about 0.3% to about 2%, about 0.1% to about 2%, or from about 0.05% to about 1% by volume. In some embodiments, the fragrance agent comprises peppermint oil. In some embodiments, the fragrance agent comprises spearmint oil. In some embodiments, the fragrance agent comprises lavender oil. In some embodiments, the fragrance agent comprises Fruit acids used in the present compositions perform multiple tasks in that they not only serve to enhance microbial inhibition property, but also impart stability, enhance fragrance, regulate pH, and impart anti oxidant properties to the present compositions. In some embodiments, the fruit acids function as a preservative. Thus, depending on their function, in various embodiments, the amount of fruit acids in the composition is in the range of about 0.01% to about 10% by weight. In some embodiments, the amount of fruit acids in the composition is in the range of about 0.1% to about 5% by weight. In some embodiments, the amount of fruit acids in the composition is in the range of about 1% to about 4% by weight. In some embodiments, the amount of fruit acids in the composition is in the range of about 2% to about 4% by weight. In other embodiments, the amount of fruit acids in the composition is in the range of about 0.5% to about 2.5% by weight. In some embodiments, the fruit acid is citric acid. In some embodiments, the amount of fruit acids in the composition is in the range of about 0.01% to about 10% by volume. In some embodiments, the amount of fruit acids in the composition is in the range of about 0.1% to about 5% by volume. In some embodiments, the amount of fruit acids in the composition is in the range of about 1% to about 4% by volume. In some embodiments, the amount of fruit acids in the composition is in the range of about 2% to about 4% by volume. In other embodiments, the amount of fruit acids in the composition is in the range of about 0.5% to about 2.5%, about 0.5% to about 2% or about 0.3 to about 2% by volume In some embodiments, the fruit acid is citric acid.

In some embodiments, the compositions may include additional additives such as thickeners, preservatives, emulsifiers, coloring agents, fragrance agents, humectants, stabilizers, pH regulators, antioxidants, conditioners, softeners, skin protectants, skin & hair nutrients, butters, surfactants essential fatty acids, collagen, elastin, keratin and other suitable additives. In some embodiments, the additives are natural products and do not contain harsh chemicals. For example, sodium bicarbonate, which functions as an odor neutralizer, may be used as an additive in the deodorant compositions.

In some embodiments, the composition may further include a moisturizer such as lanolin, alpha hydroxy acids (e.g., glycolic acid, lactic acid, etc.), urea, mineral oil, stearic acid, propylene glycol, glycerin, etc. Lanolin functions as a moisturizer, an emollient and an emulsifier. Thus, depending on its function, in various embodiments, the amount of lanolin in the composition is in the range of about 0.01% to about 10% by weight. In some embodiments, the amount of lanolin in the composition is in the range of about 0.1% to about 5% by weight. In some embodiments, the amount of lanolin in the composition is in the range of about 1% to about 4% by weight. In some embodiments, the amount of lanolin in the composition is in the range of about 2% to about 4% by weight. In some embodiments, the amount of lanolin in the composition is in the range of about 0.01% to about 10% by volume. In some embodiments, the amount of lanolin in the composition is in the range of about 0.1% to about 5% by volume. In some embodiments, the amount of lanolin in the composition is in the range of about 1% to about 4% by volume. In some embodiments, the amount of lanolin in the composition is in the range of about 2% to about 4% by volume. In some embodiments, the amount of lanolin in the composition is in the range of 0.1% to about 5%, from about 0.3% to about 4% or from about 0.5% to about 2% by volume.

The present compositions may also contain additional essential oils or natural products which perform multiple functions. Thus, for example, the composition may further include cinnamon oil, which not only increases the antimicrobial potential of the compositions, but also functions as an antioxidant, a preservative and a fragrance agent. However, cinnamon oil being a hot oil should is typically not used in very high concentrations for compositions to be used on sensitive skin surfaces. Thus, depending on its function, in various embodiments, the amount of cinnamon oil in the composition is in the range of about 0.001% to about 5% by weight. In some embodiments, the amount of cinnamon oil in the composition is in the range of about 0.01% to about 2% by weight. In some embodiments, the amount of cinnamon oil in the composition is in the range of about 0.1% to about 0.9% by weight. In some embodiments, the amount of cinnamon oil in the composition is in the range of about 0.5% to about 0.8% by weight. In some embodiments, the amount of cinnamon oil in the composition is in the range of about 0.001% to about 5% by volume. In some embodiments, the amount of cinnamon oil in the composition is in the range of about 0.01% to about 2% by volume. In some embodiments, the amount of cinnamon oil in the composition is in the range of about 0.05% to about 1.5% by volume. In some embodiments, the amount of cinnamon oil in the composition is in the range of about 0.5% to about 0.8% by volume. In some embodiments, the amount of cinnamon oil in the composition is in the range of about 0.1% to about 1% by volume.

In some embodiments, the composition may further include a thickener, such as a naturally derived thickener such as polysaccharides like guar gum and xanthan gum. In some embodiments, the amount of thickener in the composition is in the range of about 0.1% to about 5% by weight. In some embodiments, the amount of thickener in the composition is in the range of about 0.05% to about 3% by weight. In some embodiments, the amount of thickener in the composition is in the range of about 1% to about 2% by weight. In some embodiments, the thickener is xanthan gum. In some embodiments, the amount of thickener in the composition is in the range of about 0.1% to about 5% by volume. In some embodiments, the amount of thickener in the composition is in the range of about 0.05% to about 3% by volume. In some embodiments, the amount of thickener in the composition is in the range of about 1% to about 2% by volume. In some embodiments, the thickener is xanthan gum. In some embodiments, xanthan gum is present in the composition in a range of 0.1% to about 3%, from about 0.2% to about 2.5% or from about 0.3 to about 2% by volume.

The compositions described in the present technology further include water. In some embodiments, the compositions further comprise sufficient water to make 100% by weight. In some embodiments, the composition comprises about 50% to about 99%, about 60% to about 98%, about 70% to about 97%, about 80% to about 96%, about 90% to about 95% by weight water. In other embodiments, the composition comprises about 90% to about 95% by weight water. In some embodiments, the compositions further comprise sufficient water to make 100% by volume. In some embodiments, the composition comprises about 50% to about 99%, about 60% to about 98%, about 70% to about 97%, about 80% to about 96%, about 90% to about 95% by volume water. In other embodiments, the composition comprises about 90% to about 95% by volume water.

The compositions, according to the present technology, include both diluted and concentrated forms which differ only in the relative proportion of water to that of other ingredients in the compositions. While the concentrated form of the compositions may be used in their original form for heavy cleaning applications, in some embodiments, a prescribed dilution may be required for cleaning and/or disinfection. These may be easily prepared by diluting measured amounts of the concentrated compositions in water, by the consumer or other end user, in certain volume ratios of concentrated composition to water, and optionally agitating the same to ensure even mixing of the concentrate in the water. The actual dilution selected is in part determinable by the degree and amount of microbes, dirt and grime to be removed from the surfaces, the amount of scrubbing imparted to remove the same, as well as the observed efficacy of the particular dilution.

The present compositions can be formulated into a wide variety of products. These include, but are not limited to, personal products such as hand-sanitizers, antiseptics, soaps, skin creams, lotions, shampoos, shaving creams, conditioners, deodorants, ointments, dental products, hand wash, air fresheners and hand gels; insect repellant, household cleaners such as dish or laundry soaps, commercial cleaners, etc. Still further, the present compositions may be incorporated or impregnated into plastics to preserve the material and provide antimicrobial protection on its surfaces or formulated as a natural preservative into food products, cosmetics or personal care products. In some embodiments, the composition is a hand-sanitizer. In some embodiments, the composition is a deodorant. In some other embodiments, the composition is a dry shampoo or a scalp refresher.

In one aspect, the present technology provides a hand-sanitizer composition which includes (a) about 1% to about 4% by weight of palmarosa oil, (b) about 0.5% to about 2.5% by weight of tea tree oil, (c) about 1% to about 4% by weight of jojoba oil, (d) about 5% to about 15% by weight of coconut oil, (e) about 1% to about 4% by weight of citric acid, and (f) about 1% to about 4% by weight of lanolin. In another aspect, the present technology provides an aqueous hand-sanitizer composition which includes (a) about 1% to about 4% by volume of palmarosa oil, (b) about 0.5% to about 2.5% by volume of tea tree oil, (c) about 1% to about 4% by volume of jojoba oil, (d) about 5% to about 15% by volume of coconut oil, (e) about 1% to about 4% by volume of citric acid, (f) about 1% to about 4% by volume of lanolin and in some embodiments, (g) water to make 100% volume.

In some embodiments, the hand-sanitizer further includes a thickener and one or more fragrance agents. In some embodiments, the thickener is xanthan gum. In some embodiments, the fragrance agent is selected from cinnamon oil and peppermint oil or a combination thereof. In some embodiments, the fragrance agent is cinnamon oil. In other embodiments, the fragrance agent is peppermint oil. In some embodiments, the amount of fragrance agent in the composition is in the range of about 0.1% to about 4% by weight. In other embodiments, the amount of fragrance agent in the composition is in the range of about 0.3% to about 2% by weight. In some embodiments, the compositions further comprise sufficient water to make 100% by weight. In some embodiments, the amount of fragrance agent in the composition is in the range of about 0.1% to about 4% by volume. In other embodiments, the amount of fragrance agent in the composition is in the range of about 0.3% to about 2% by volume. In some embodiments, the compositions further comprise sufficient water to make 100% by volume.

In some embodiments, the hand-sanitizer composition includes (a) about 0.5% to about 2% by weight of palmarosa oil, (b) about 0.3% to about 2% by weight of tea tree oil, (c) about 0.5% to about 2% by weight of jojoba oil, (d) about 1% to about 5% by weight of coconut oil, (e) about 0.5% to about 2% by weight of citric acid, and (f) about 0.5% to about 2% by weight of lanolin. In some embodiments, the hand-sanitizer composition includes (a) about 0.5% to about 2% by volume of palmarosa oil, (b) about 0.3% to about 2% by volume of tea tree oil, (c) about 0.5% to about 2% by volume of jojoba oil, (d) about 1% to about 5% by volume of coconut oil, (e) about 0.5% to about 2% by volume of citric acid, and (f) about 0.5% to about 2% by volume of lanolin.

In some embodiments, the hand-sanitizer further includes a thickener and one or more fragrance agents. In some embodiments, the thickener is xanthan gum. In some embodiments, the fragrance agent is selected from cinnamon oil and peppermint oil or a combination thereof. In some embodiments, the fragrance agent is cinnamon oil. In other embodiments, the fragrance agent is peppermint oil. In some embodiments, the amount of fragrance agent in the composition is in the range of about 0.1% to about 4% by weight. In other embodiments, the amount of fragrance agent in the composition is in the range of about 0.3% to about 2% by weight. In other embodiments, the amount of fragrance agent in the composition is in the range of about 0.1% to about 1% by weight. In some embodiments, the compositions further comprise sufficient water to make 100% by weight. In some embodiments, the amount of fragrance agent in the composition is in the range of about 0.1% to about 4% by volume. In other embodiments, the amount of fragrance agent in the composition is in the range of about 0.3% to about 2% by volume. In other embodiments, the amount of fragrance agent in the composition is in the range of about 0.1% to about 1% by volume. In some embodiments, the compositions further comprise sufficient water to make 100% by volume.

In some embodiments, the hand-sanitizer composition includes (a) about 0.5% to about 2% by volume of palmarosa oil, (b) about 0.3% to about 2% by volume of tea tree oil, (c) about 0.5% to about 2% by volume of jojoba oil, (d) about 1% to about 5% by volume of coconut oil, (e) about 0.1% to about 1% by volume of cinnamon oil (f) about 0.1% to about 1% by volume of peppermint oil (g) about 0.5% to about 2% by volume of citric acid, and (h) about 0.5% to about 2% by volume of lanolin.

The hand-sanitizing composition can be formulated in any commercially available or other form known in the art. For example, the hand-sanitizer can be formulated as gels, foams, sprays, wipes, liquids, soaps. These compositions can be sold as dispensers, refills, bars, in individual or bulk packets of wipes, etc. In some embodiments, the present compositions may be formulated to be dispersed from a ready-to-use dispenser system. For instance, the compositions may be dispelled from a trigger or finger pump bottle, a squeeze bottle or a pressurized sprayer to produce a spray, fog or foam. In other embodiments, the present compositions may also be incorporated into wipes, i.e., a towelette form, or a gel or lotion carrier to treat a variety of surfaces. The wipes may be packaged individually or in bulk for individual distribution. Further, the compositions may be incorporated into other formulations or carriers having antimicrobial or disinfecting properties.

In another aspect, the present technology provides a deodorant composition which includes (a) about 1% to about 4% by volume of palmarosa oil, (b) about 2% to about 10% by volume of jojoba oil, (c) about 1% to about 4% by volume of lavender oil, (d) about 0.5% to about 2.5% by volume of citric acid. In some embodiments, the deodorant further includes a thickener and a fragrance agent. In some embodiments, the thickener is xanthan gum. In some embodiments, the compositions further comprise sufficient water to make 100% by volume.

In another embodiment, the deodorant composition includes (a) about 0.5% to about 2% by volume of palmarosa oil, (b) about 1% to about 4% by volume of jojoba oil, (c) about 0.5% to about 2% by volume of lavender oil, (d) about 0.3% to about 2% by volume of citric acid. In some embodiments, the deodorant further includes a thickener and a fragrance agent. In some embodiments, the thickener is xanthan gum. In some embodiments, the compositions further comprise sufficient water to make 100% by volume.

In some embodiments, the deodorant composition includes (a) about 0.5% to about 2% by volume of tea tree oil, (b) about 0.5% to about 2% by volume of palmarosa oil, (c) about 0.5% to about 2% by volume of jojoba oil, (d) about 0.5% to about 2% by volume of coconut oil, (e) about 0.3% to about 2% by volume of peppermint oil, (e) about 0.8% to about 3% by volume of lavender oil, and (f) about 0.5% to about 2.5% by volume of citric acid. In some embodiments, the deodorant further includes a thickener, an odor neutralizer and a fragrance agent. In some embodiments, the thickener is xanthan gum. In some embodiments, the odor neutralizer is sodium bicarbonate. In some embodiments, the compositions further comprise sufficient water to make 100% by volume.

In some embodiments, the deodorant composition includes (a) about 0.5% to about 2% by volume of tea tree oil, (b) about 0.5% to about 2% by volume of palmarosa oil, (c) about 0.5% to about 2% by volume of jojoba oil, (d) about 0.5% to about 2% by volume of coconut oil, (e) about 0.3% to about 2% by volume of peppermint oil, (e) about 0.1% to about 2% by volume of spearmint oil, and (f) about 0.5% to about 2.5% by volume of citric acid. In some embodiments, the deodorant further includes a thickener, an odor neutralizer and a fragrance agent. In some embodiments, the thickener is xanthan gum. In some embodiments, the odor neutralizer is sodium bicarbonate. In some embodiments, the compositions further comprise sufficient water to make 100% by volume. In some embodiments, about 0.5% to about 2.5%, or about 0.3% to about 2% by volume of clary sage oil is included in a deodorant composition.

The deodorant composition can be formulated in any commercially available or other form known in the art. For example, the deodorant can be formulated as solids, liquids, aerosols, gels, and powders.

In yet another aspect, the present technology provides a scalp refresher composition. In some embodiments, the scalp refresher includes one or more essential oils, and citric acid. In some embodiments, the scalp refresher includes sweet orange oil, grapefruit oil, lavender oil, rosemary oil, sandalwood oil, citric acid and a fragrance agent. In some embodiments, the fragrance agent comprises lavender oil, peppermint oil, spearmint oil or a combination thereof. In one embodiment, the scalp refresher includes (a) about 0.8% to about 3% by volume of sweet orange oil, (b) about 0.5% to about 2% by volume of grapefruit oil, (c) about 0.1% to about 2% by volume of lavender oil, (d) about 0.05% to about 1% by volume of rosemary oil, (e) about 0.05% to about 1% by volume of sandalwood oil, (f) about 0.05% to about 1% by volume of peppermint oil, and (g) about 0.5% to about 2.5% by volume of citric acid. In some embodiments, the scalp refresher includes palmarosa oil and tea tree oil. In some embodiments, the scalp refresher further includes a thickener. In some embodiments, the thickener is xanthan gum. In some embodiments, the compositions further comprise sufficient water to make 100% by volume.

The scalp refresher composition can be formulated in any commercially available or other form known in the art. For example, the scalp refresher can be formulated as solids, liquids, aerosols, gels, and powders. The scalp refresher composition can be used to condition and stimulate the scalp and thereby promote hair growth. The scalp refresher composition can also be used to prevent the growth of bacteria and germs which cause dry scalp conditions such as dandruff and itching of scalp. The refresher also eliminated odor and, therefore, can be used in place of a shampoo.

In some embodiments, the present compositions include all naturally derived ingredients which are free of harsh chemicals. Specifically, the present compositions contain non-toxic and biodegradable ingredients. For example, the hand sanitizers made from present compositions are free of harmful chemicals such as alcohol, triclosan or benzethionium chloride. The deodorants made from present compositions are free of harsh chemicals such as aluminum compounds and parabens, among other things. The present compositions are gentle and suitable for use on sensitive skin surfaces because they do not contain high-quantities of hot essential oils, such as thyme and oregano, which have high phenols that are harmful to the skin in general and may severely irritate sensitive skin. These compositions are, therefore, gentle enough to be used in all forms of compositions, e.g., deodorants used under the arms. Most significant, the present compositions can be produced without the use of harsh surfactants such as sodium lauryl sulfate or sodium dioctyl sulfosuccinate, which are used in several commercial natural products to homogenize them and improve their stability and shelf life.

Since the components of the present cleaning, disinfecting and deodorizing compositions originate from natural sources, these compositions are readily highly biodegradable and can be used without concern of environmental build up. It has been found that the particular combination of essential oils, namely palmarosa oil, along with other oils selected from tea tree oil, jojoba oil, coconut oil, clary sage oil, and lavender oil, with a fruit acid such as citric acid, dissolved or dispersed in the water, each at particular concentration ranges, together exhibit unexpectedly good cleaning property and good disinfecting property against a broad spectrum of microorganisms. The present compositions have been found to be effective against microorganisms, and it is believed that the microorganisms are not expected to develop resistance to the formulations over time.

Biological Activity

A comprehension of the vast benefits of the antimicrobial compositions of the present technology entails an understanding of the various microbes against which the present compositions are effective. The present compositions may be used as a fungicide, germicide, virucide, bactericide or combinations thereof. Bacteria found on various surfaces, as well as human skin, include resident and transient bacteria which may further include Gram-positive bacteria and Gram-negative bacteria. Gram-positive bacteria include pathogens such as *Staphylococcus aureus, Pseudomonas aeruginosa, Streptococcus pyogenes* and *Clostridium botulinum*. Gram-negative bacteria include pathogens such as *Salmonella, Escherichia coli, Klebsiella, Haemophilus, Proteus* and *Shigella dysenteriae*. Apart from bacteria, the present compositions are also active against a broad range of other pathogens such as Influenza A virus, adenovirus, *Giardia Muris, Aspergillus Fumigatus, Candida albicans, Cryptosporidium*, etc.

In some embodiments, the present compositions utilize the most effective essential oils and fruit acids in very specific concentrations to provide a synergistic strong antimicrobial effect against a broad range of microbial species. The present compositions are thus effective against one or more microbes selected from the group consisting of *Escherichia coli, Pseudomonas aeruginosa, Staphylococcus aureus*, and *Can-*

*dida albicans*. Suitable techniques known in the art can be employed to detect the antimicrobial activity, toxicity and safety data of the present compositions. Such methods include, for example, studying the time kill assay for the antimicrobial agents using a wide variety of microorganisms. In the time kill assay, the rate at which various concentrations of an antimicrobial composition kill a bacterium over time is studied.

In one aspect, the present technology relates to methods of preparing the antimicrobial compositions. The present compositions may be formulated by conventional procedures known to one skilled in the art. For example, the compositions can be formulated by combining the individual ingredients, such as essential oils, fruit acids, other additives and water together. The combined ingredients are then agitated or mixed, either manually or using a homogenizer, until a macroemulsified or microemulsified solution is formed.

The present technology also relates to methods of using the antimicrobial compositions. In one aspect, a method for disinfection and/or cleaning a surface using the present compositions is provided. The method includes contacting the surface with the compositions of the present technology. In some embodiments, the method includes contacting a surface with a composition which includes (a) 1% to about 4% by volume of palmarosa oil, (b) one or more of about 0.5% to about 2.5% by volume of tea tree oil, about 1% to about 4% by volume of jojoba oil, about 5% to about 15% by volume of coconut oil, and about 1% to about 4% by volume of citric acid, and (c) sufficient water to make 100% by volume.

The present technology also relates to methods of using the antimicrobial compositions. In one aspect, a method for disinfection and/or cleaning a surface using the present compositions is provided. The method includes contacting the surface with the compositions of the present technology. In some embodiments, the method includes contacting a surface with a composition which includes (a) 0.5% to about 2% by volume of palmarosa oil, (b) one or more of about 0.3% to about 2% by volume of tea tree oil, about 0.5% to about 2% by volume of jojoba oil, about 0.8% to about 5% by volume of coconut oil, and about 0.5% to about 2% by volume of citric acid, and (c) sufficient water to make 100% by volume.

The antimicrobial compositions and methods of the present technology can be used as a one-step cleaning, disinfecting, deodorizing and sanitizing product on a wide variety of surfaces known in the art. The compositions may be used directly on the surfaces to be cleaned, disinfected, deodorized and sanitized without prior wiping of the surfaces with water to cleanse the surfaces. In some embodiments, the surface is selected from the group consisting of soft surface, hard surface, porous surface, food substance and skin. Hard, non-porous surfaces include, but are not limited to, medical instruments, countertops including kitchen and bathroom counters, eating utensils, bathroom fixtures such as sinks and toilets, tiles, toys, phones, remote controls, keyboards, doorknobs, floors, walls, windows, furniture, appliances, high chair trays, cribs, shopping carts, etc. Soft surfaces include, but are not limited to, carpeting, upholstery and other fabrics. In some embodiments, the compositions can be used as food additives. In some embodiments, the surface is skin.

Since only natural, safe ingredients are included in the present compositions, they do not need to be wiped off or rinsed off after being applied to the various surfaces. This allows for longer contact with the surface area bearing the microorganisms and, as such, ensures a higher killing rate and continuous germ control for extended periods of time where desired. Further, since the present compositions do not require wiping or rinsing to remove any residues, they are also convenient and easy to use. In addition, the present compositions are non-corrosive, non-flammable, non-reactive, readily biodegradable, and have a very low volatile organic compound level of less than 1%.

While hand-sanitizers and deodorants are specified in certain embodiments of the present disclosure, the compositions can be included in any type of cosmetic, personal care, health care, food, paint or other industrial composition.

As will be readily apparent to one of ordinary skill in the art, the concentration of a given ingredient can be increased or decreased beyond the range disclosed and the effect of the increased or decreased concentration can be determined using only routine experimentation. The optimal final concentrations for ingredients are typically identified by the nature of formulation and the desired end use of the composition.

The present technology, thus generally described, will be understood more readily by reference to the following examples which are provided by way of illustration and are not intended to be limiting in any way.

EXAMPLES

The present technology is further illustrated by the following examples which should not be construed as limiting in any way.

Illustrative compositions of present technology, for use as a hand sanitizing composition, deodorant compositions and scalp refresher (e.g., a dry shampoo), are described in Examples 1-6. It is understood that larger batches of each of the compositions can be made simply by increasing the amount of each component by the same factor. For example, a double-batch can be made by increasing the amount of each component by 2; a triple batch can be made by increasing the amount of each component by three, a ten-fold batch can be made by increasing the amount of each component by 10, etc. The ratio of components remains essentially constant while the volume of each increases. As noted above, the compositions can be formulated as concentrates. In some embodiments, the concentrates include no water or water up to 95%, 96%, 97%, 98% or 99% of the amount provided in the formulations described below.

Additionally or alternatively, in some embodiments, the individual components are combined and water is added such that the final volume is 1 cup. Except for the water, in such embodiments, the ratio of the components will remain essentially the same.

Example 1

Hand-Sanitizer Composition (A)

TABLE 1

| Ingredient | Quantity | Ratio |
|---|---|---|
| Palmarosa oil | ½ tsp | 4 |
| Tea tree oil | ¼ tsp | 2 |
| Jojoba oil | ½ tsp | 4 |
| Coconut oil | 1¼ tsp | 10 |
| Cinnamon oil | ⅛ tsp | 1 |
| Citric acid | ½ tsp | 4 |
| Lanolin | ½ tsp | 4 |
| Xanthan gum | ¼ tsp | 2 |
| Water | 1 cup | 384 |

Example 2

Hand-Sanitizer Composition (B)

TABLE 2

| Ingredient | Quantity | Ratio |
| --- | --- | --- |
| Palmarosa oil | ½ tsp | 4 |
| Tea tree oil | ¼ tsp | 2 |
| Jojoba oil | ½ tsp | 4 |
| Coconut oil | 1¼ tsp | 10 |
| Cinnamon oil | ⅛ tsp | 1 |
| Citric acid | ½ tsp | 4 |
| Lanolin | ½ tsp | 4 |
| Xanthan gum | ¼ tsp | 2 |
| Peppermint oil | ⅛ tsp | 1 |
| Water | 1 cup | 384 |

Example 3

Deodorant Composition (A)

TABLE 3

| Ingredient | Quantity | Ratio |
| --- | --- | --- |
| Palmarosa oil | ½ tsp | 2 |
| Jojoba oil | 1 tsp | 4 |
| Lavender oil | ½ tsp | 2 |
| Clary sage oil (optional) | ¼ tsp | 1 |
| Citric acid | ¼ tsp | 1 |
| Xanthan gum | ¼ tsp | 1 |
| Water | 1 cup | 192 |

Example 4

Deodorant Composition (B)

TABLE 4

| Ingredient | Quantity | Ratio |
| --- | --- | --- |
| Tea Tree oil | 0.5 tsp | 2 |
| Palmarosa oil | 0.5 tsp | 2 |
| Jojoba oil | 0.5 tsp | 2 |
| Coconut oil | 0.5 tsp | 2 |
| Peppermint oil or spearmint oil | 0.25 tsp | 1 |
| Lavender oil | 0.6 tsp | 2.4 |
| Sodium Bicarbonate | 0.5 tsp | 2 |
| Xanthan gum | 0.25 tsp | 1 |
| Citric acid | 0.4 tsp | 1.6 |
| Water | 1 cup | 192 |

Example 5

Deodorant Composition (C)

TABLE 5

| Ingredient | Quantity | Ratio |
| --- | --- | --- |
| Tea Tree oil | 0.5 tsp | 2 |
| Palmarosa oil | 0.5 tsp | 2 |
| Jojoba oil | 0.5 tsp | 2 |
| Coconut oil | 0.5 tsp | 2 |
| Peppermint oil | 0.25 tsp | 1 |
| Spearmint oil | 0.2 tsp | 0.8 |
| Sodium Bicarbonate | 0.5 tsp | 2 |
| Xanthan gum | 0.25 tsp | 1 |
| Citric acid | 0.4 tsp | 1.6 |
| Water | 1 cup | 192 |

TABLE 5-continued

Example 6

Scalp Refresher Composition

TABLE 6

| Ingredient | Quantity | Ratio |
| --- | --- | --- |
| Sweet Orange oil | 0.6 tsp | 6 |
| Grapefruit oil | 0.4 tsp | 4 |
| Lavender oil | 0.2 tsp | 2 |
| Rosemary oil | 0.1 tsp | 1 |
| Sandalwood oil | 0.1 tsp | 1 |
| Peppermint oil | 0.1 tsp | 1 |
| Xanthan gum | 0.3 tsp | 3 |
| Citric acid | 0.2 tsp | 2 |
| Water | 1 cup | 480 |

The individual ingredients, in the examples above, are measured and mixed together until they form a homogeneous composition.

Example 7

Biological Activity

The sanitizing compositions were successfully tested against *Staphylococcus aureus* and *Pseudomonas aeruginosa* using the standard time kill assay for antimicrobial agents. *Staphylococcus aureus* is known to have the most resistance or known microbacterial organisms for disinfectant evaluation. As an illustration, the time kill assay was performed for the sample hand-sanitizer composition of Example 1 against two microorganisms, namely *Staphylococcus aureus* and *Pseudomonas aeruginosa*. The data in Tables 7, 8, 9, and 10 shows that the listed essential oils in the compositions exhibited antimicrobial activity by passing the test used in the evaluation of such activity.

| Assay: Time Kill Assay for Antimicrobial Agents | | |
| --- | --- | --- |
| Test Organism | ATCC# | Culture Medium |
| *Staphylococcus aureus* | 6538 | Tryptic Soy Agar with 5% Sheep Blood |
| *Pseudomonas aeruginosa* | 15442 | Tryptic Soy Agar with 5% sheep Blood |

The microorganisms used in this study were obtained from the American Type Culture Collection (ATCC), Manassas, Va.
Recovery Media
Neutralizer: Letheen Broth with 0.07% Lecithin+0.5% Tween 80
Agar Plate Medium: Tryptic Soy Agar with 5% Sheep Blood (BAP)

Exposure Times: 30 seconds, 1 minute, 2 minutes and 5 minutes
Exposure Temperature Ambient temperature (19° C.)
Dilution: Ready to use (RTU)

Experimental Design.

A suspension of bacterial cells was exposed to the test substance for specified exposure times. After exposure, an aliquot of the suspension was transferred to a neutralizer and assayed for survivors. Appropriate culture purity, neutralizer sterility, initial suspension population and neutralization controls were performed.

Study Results.

The following results from controls confirmed study validity:

TABLE 7

CONTROL RESULTS

| Type of Control | Results | |
|---|---|---|
| | *Staphytococcus aureus* (ATCC 6538) | *Pseudomonas aeruginosa* (ATCC 15442) |
| Purity Control | Pure | Pure |
| Neutralizer Sterility Control | No Growth | |

TABLE 8

NEUTRALIZATION CONTROLS

| Test Substance | Test Organism | Organism Dilution | Average Number of Survivors Recovered | | $\pm 1.0 \log_{10}$ Pass/Fail |
|---|---|---|---|---|---|
| | | | With Product | Numbers Control | |
| 1a | *Staphylococcus aureus* (ATCC 6538) | $10^{-7}$ | 6.4 | 2.4 | −0.2 |

TABLE 8-continued

NEUTRALIZATION CONTROLS

| Test Substance | Test Organism | Organism Dilution | Average Number of Survivors Recovered | | $\pm 1.0 \log_{10}$ Pass/Fail |
|---|---|---|---|---|---|
| | | | With Product | Numbers Control | |
| | *Pseudomonas aeruginosa* (ATCC) | | 3.7 | 4.5 | 0.0 |

TABLE 9

TEST RESULTS
Test Substance: 1a

| DILUTION | Exposure Time | | | |
|---|---|---|---|---|
| | 30 seconds | 1 minute | 2 minutes | 5 minutes |
| | Number of Survivors | | | |
| Test Organism: *Staphylococcus aureus* (ATCC 6538) | | | | |
| $10^0$ (1.00 mL plated) | 51.32 | 0.0 | 0.0 | 0.0 |
| $10^{-1}$ | 9.9 | 0.0 | 0.0 | 0.0 |
| $10^{-2}$ | 1.1 | 0.0 | 0.0 | 0.0 |
| $10^{-3}$ | 0.0 | 0.0 | 0.0 | 0.0 |
| $10^{-4}$ | 0.0 | 0.0 | 0.0 | 0.0 |
| Test Organism: *Pseudomonas aeruginosa* (ATCC 15442) | | | | |
| $10^0$ (1.00 mL plated) | 0.0 | 0.0 | 0.0 | 0.0 |
| $10^{-1}$ | 0.0 | 0.0 | 0.0 | 0.0 |
| $10^{-2}$ | 0.0 | 0.0 | 0.0 | 0.0 |
| $10^{-3}$ | 0.0 | 0.0 | 0.0 | 0.0 |
| $10^{-4}$ | 0.0 | 0.0 | 0.0 | 0.0 |

TABLE 10

CALCULATED DATA
Test Substance: 1a

| Test Organism | Exposure Time | Test Population Control CFU/mL* ($\log_{10}$) | Number of Survivors CFU/mL* | $\log_{10}$ Number of Survivors | Percent Reduction | $\log_{10}$ Reduction |
|---|---|---|---|---|---|---|
| *Staphylococcus aureus* (ATCC 6538) | 30 seconds | $1.27 \times 10^6$ (6.104) | $4.2 \times 10^2$ | 2.62 | >99.9% | 3.48 |
| | 1 minute | | $<1 \times 10^1$ | <1.0 | >99.999% | >5.1 |
| | 2 minutes | | $<1 \times 10^1$ | <1.0 | >99.999% | >5.1 |
| | 5 minutes | | $<1 \times 10^1$ | <1.0 | >99.999% | >5.1 |
| *Pseudomonas aeruginosa* (ATCC 15442) | 30 seconds | $1.74 \times 10^6$ (6.241) | $<1 \times 10^1$ | <1.0 | >99.999% | >5.2 |
| | 1 minute | | $<1 \times 10^1$ | <1.0 | >99.999% | >5.2 |
| | 2 minutes | | $<1 \times 10^1$ | <1.0 | >99.999% | >5.2 |
| | 5 minutes | | $<1 \times 10^1$ | <1.0 | >99.999% | >5.2 |

*CFU = Colony Forming Units per mL of test mixture

Control Results.

All data measurements/controls including neutralization confirmation, culture purity, test population, and neutralizer sterility controls performed within acceptance criteria.

Analysis.

Under the conditions of this study, 1a demonstrated >99.9% (3.48 $\log_{10}$) reduction of *Staphylococcus aureus* survivors after a 30 second exposure and demonstrated >99.999% (>5.1 $\log_{10}$) reduction of *Staphylococcus aureus* survivors following a one, two and five minute exposure when tested at ambient temperature (19.0° C.).

Under the condition of this study, 1a demonstrated >99.999% (>5.2 $\log_{10}$) reduction of *Pseudomonas aeruginosa* survivors following a 30 second, one, two and five minute exposure when tested at ambient temperature (19° C.).

The study demonstrated that the present compositions exhibit excellent antimicrobial activity against tested microorganisms. This study can be extrapolated to test the activity of the present compositions against other microorganisms.

While certain embodiments have been illustrated and described, it should be understood that changes and modifications can be made therein in accordance with ordinary skill in the art without departing from the technology in its broader aspects as defined in the following claims.

The embodiments, illustratively described herein, may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described, or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like, includes the number recited and refers to ranges which can be subsequently broken down into subranges as discussed above. Finally, as will be understood by one skilled in the art, a range includes each individual member.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An antimicrobial composition comprising one or more essential oils and one or more fruit acids, wherein
    at least one essential oil is palmarosa oil, and wherein the antimicrobial composition comprises:
        (a) about 0.01% to about 15% by volume of palmarosa oil,
        (b) about 0.01% to about 10% by volume of tea tree oil,
        (c) about 0.01% to about 15% by volume of jojoba oil,
        (d) about 0.01% to about 30% by volume of coconut oil,
        (e) about 0.01% to about 10% by volume of a fruit acid selected from the group consisting of citric acid, glycolic acid, lactic acid, malic acid, tartaric acid and acetic acid;
    and wherein
    the composition possesses antimicrobial activity;
    the composition is alcohol-free; and
    the composition is free of any surfactant.

2. The antimicrobial composition of claim 1, comprising one or more components selected from a group consisting of emollients, moisturizers, preservatives, thickeners, fragrance agents and homogenizers.

3. The antimicrobial composition of claim 2, wherein the emollient is lanolin.

4. The antimicrobial composition of claim 2, wherein the thickener is xanthan gum.

5. The antimicrobial composition of claim 1, comprising:
    (a) 0.5% to 2% by volume of palmarosa oil,
    (b) 0.3% to 2% by volume of tea tree oil,
    (c) 0.5% to 2% by volume of jojoba oil,
    (d) 1% to 5% by volume of coconut oil,
    (e) 0.1% to 1% by volume of cinnamon oil,
    (f) 0.1% to 1% by volume of peppermint oil,
    (g) 0.5% to 2% by volume of citric acid,
    (h) 0.5% to 2% by volume of lanolin, and
    (i) 0.3% to 2% by volume of xanthan gum.

6. The antimicrobial composition of claim 1, wherein the ratio of the components is as follows:

| | |
|---|---|
| Palmarosa oil | 4: |
| Tea tree oil | 2: |
| Jojoba oil | 4: |
| Coconut oil | 10: |
| Cinnamon oil | 1: |
| Citric acid | 4: |
| Lanolin | 4: |
| Xanthan gum | 2: |
| Peppermint oil | 1. |

7. The antimicrobial composition of claim 1, wherein the composition is a hand-sanitizer.

8. The antimicrobial composition of claim 1, wherein the composition is a deodorant.

9. The antimicrobial deodorant composition of claim 8 comprising:
 (a) 0.5% to 2% by volume of palmarosa oil,
 (b) 1% to 4% by volume of jojoba oil,
 (c) 0.5% to 2% by volume of lavender oil, and
 (d) 0.3% to 2% by volume of citric acid.

10. The antimicrobial deodorant composition of claim 9, further comprising a thickener and a fragrance agent.

11. The antimicrobial deodorant composition of claim 10, wherein the thickener is xanthan gum and the fragrance agent is selected from cinnamon oil and peppermint oil or a combination thereof.

12. The antimicrobial deodorant composition of claim 8 comprising:
 (a) 0.5% to 2% by volume of tea tree oil,
 (b) 0.5% to 2% by volume of palmarosa oil,
 (c) 0.5% to 2% by volume of jojoba oil,
 (d) 0.5% to 2% by volume of coconut oil,
 (e) 0.3% to 2% by volume of peppermint oil or spearmint oil,
 (f) 0.8% to 3% by volume of lavender oil, and
 (g) 0.5% to 2.5% by volume of citric acid.

13. The antimicrobial deodorant composition of claim 12, further comprising sodium bicarbonate and xanthan gum.

14. The antimicrobial deodorant composition of claim 8 comprising:
 (a) 0.5% to 2% by volume of tea tree oil,
 (b) 0.5% to 2% by volume of palmarosa oil,
 (c) 0.5% to 2% by volume of jojoba oil,
 (d) 0.5% to 2% by volume of coconut oil,
 (e) 0.3% to 2% by volume of peppermint oil,
 (f) 0.1% to 2% by volume of spearmint oil, and
 (g) 0.5% to 2.5% by volume of citric acid.

15. The antimicrobial deodorant composition of claim 14, further comprising sodium bicarbonate and xanthan gum.

16. A scalp refresher composition comprising:
 (a) 0.8% to 3% by volume of sweet orange oil,
 (b) 0.5% to 2% by volume of grapefruit oil,
 (c) 0.1% to 2% by volume of lavender oil,
 (d) 0.05% to 1% by volume of rosemary oil,
 (e) 0.05% to 1% by volume of sandalwood oil,
 (f) 0.05% to 1% by volume of peppermint oil, and
 (g) 0.5% to 2.5% by volume of citric acid;
and wherein
 the composition possess antimicrobial activity;
 the composition is alcohol-free; and
 the composition is free of any surfactant.

17. The antimicrobial deodorant composition of claim 8, wherein the composition comprises the following components: palmarosa oil, tea tree oil, jojoba oil, lavender oil, citric acid, xanthan gum, sodium bicarbonate and water.

18. The antimicrobial deodorant composition of claim 17, comprising:
 (a) 0.5% to 2% by volume of tea tree oil,
 (b) 0.5% to 2% by volume of palmarosa oil,
 (c) 0.5% to 2% by volume of jojoba oil,
 (d) 0.5% to 2% by volume of lavender oil, and
 (e) 0.5% to 2.5% by volume of citric acid.

19. The scalp refresher composition of claim 16, comprising tea tree oil, xanthan gum and water.

20. The scalp refresher composition of claim 19, comprising:
 (a) 0.8% to 3% by volume of sweet orange oil,
 (b) 0.5% to 2% by volume of grapefruit oil,
 (c) 0.1% to 2% by volume of lavender oil,
 (d) 0.05% to 1% by volume of rosemary oil,
 (e) 0.05% to 1% by volume of sandalwood oil,
 (f) 0.05% to 1% by volume of peppermint oil,
 (g) 0.05% to 1% by volume of tea tree oil, and
 (h) 0.5% to 2.5% by volume of citric acid.

21. The antimicrobial composition according to claim 1, wherein the composition causes about 3.48 $\log_{10}$ reduction in *Staphylcoccus aureus* after thirty seconds of contact time.

22. The antimicrobial composition according to claim 1, wherein the composition causes at least 5.2 $\log_{10}$ reduction in *Pseudomonas aeruginosa* after thirty seconds of contact time.

* * * * *